(12) United States Patent
Heischkel et al.

(10) Patent No.: US 8,471,007 B2
(45) Date of Patent: *Jun. 25, 2013

(54) METHOD FOR PRODUCING 1,3,5-TRIAZINE CARBAMATES AND UREAS

(75) Inventors: Yvonne Heischkel, Mannheim (DE); Eva Wagner, Speyer (DE); Joerg Schneider, Weinheim (DE); Reinhold Schwalm, Wachenheim (DE); Guenter Scherr, Ludwigshafen (DE); Karl Haeberle, Speyer (DE)

(73) Assignee: BASF SE, Ludwigshafen (DE)

( * ) Notice: Subject to any disclaimer, the term of this patent is extended or adjusted under 35 U.S.C. 154(b) by 1261 days.

This patent is subject to a terminal disclaimer.

(21) Appl. No.: 10/593,308

(22) PCT Filed: Apr. 8, 2005

(86) PCT No.: PCT/EP2005/003690
§ 371 (c)(1),
(2), (4) Date: Sep. 18, 2006

(87) PCT Pub. No.: WO2005/100328
PCT Pub. Date: Oct. 27, 2005

(65) Prior Publication Data
US 2007/0196668 A1    Aug. 23, 2007

(30) Foreign Application Priority Data
Apr. 14, 2004 (DE) .................... 10 2004 018 544

(51) Int. Cl.
*C07D 251/70*    (2006.01)

(52) U.S. Cl.
USPC .......................................... 544/196; 544/200

(58) Field of Classification Search
USPC ................................................ 544/196, 200
See application file for complete search history.

(56) References Cited

U.S. PATENT DOCUMENTS

| | | | |
|---|---|---|---|
| 4,939,213 A | 7/1990 | Jacobs, III et al. | |
| 5,565,243 A | 10/1996 | Mauer et al. | |
| 5,852,133 A * | 12/1998 | Gupta et al. | 525/375 |
| 6,204,382 B1 * | 3/2001 | Flood et al. | 544/194 |
| 7,169,923 B2 * | 1/2007 | Schneider et al. | 544/196 |
| 7,371,856 B2 * | 5/2008 | Schneider et al. | 544/196 |
| 7,517,474 B2 * | 4/2009 | Wagner et al. | 252/401 |
| 8,044,197 B2 * | 10/2011 | Heischkel et al. | 544/196 |

FOREIGN PATENT DOCUMENTS

| | | |
|---|---|---|
| DE | 101 51 564 | 4/2003 |
| EP | 0 305 115 | 3/1989 |
| EP | 0 359 430 | 3/1990 |
| EP | 0 366 884 | 5/1990 |
| EP | 0 473 948 | 3/1992 |
| EP | 0624577 * | 5/1994 |
| WO | 97 08235 | 3/1997 |
| WO | WO-98/18856 A1 * | 5/1998 |
| WO | WO-01/40368 A1 * | 6/2001 |
| WO | WO 03035628 A1 * | 5/2003 |

* cited by examiner

*Primary Examiner* — Venkataraman Balasubramanian
(74) *Attorney, Agent, or Firm* — Oblon, Spivak, McClelland, Maier & Neustadt, L.L.P.

(57) ABSTRACT

Process for preparing higher 1,3,5-triazine carbamates and 1,3,5-triazine ureas from lower 1,3,5-triazine carbamates.

24 Claims, No Drawings

METHOD FOR PRODUCING 1,3,5-TRIAZINE CARBAMATES AND UREAS

The present invention describes a process for preparing 1,3,5-triazine carbamates and 1,3,5-triazine ureas from other 1,3,5-triazine carbamates.

U.S. Pat. No. 4,939,213 describes the coatings formed by curing tricarbamoyltriazines with polyesterols or polyacrylates comprising active hydrogen atoms at room temperature in the presence of a curing catalyst. The catalyst disclosed comprises tin salts and also quaternary and ternary cationic salts. In examples 7 and 8 there is a description of curing at room temperature in the presence of a tin catalyst, but the reaction time is unspecified.

U.S. Pat. No. 5,565,243 describes the primer coating materials which comprise tricarbamoyltriazines having alkyl groups of up to 12 carbon atoms and resin as binder and also a topcoat material comprising polyepoxide and crosslinker, the primer coating material being curable for example with tin compounds and the topcoat material for example with secondary or tertiary amines. The examples are each cured at room temperature.

A disadvantage of these systems is that the lower alcohol eliminated from the tricarbamoyltriazines is unable to escape. Moreover, owing to increasing crosslinking of the coating, a high conversion rate is impossible to achieve through the cure. Room temperature curing, furthermore, requires long reaction times. The tricarbamoyltriazines used are prepared by reacting high-reactivity 1,3,5-triazine triisocyanate with alcohols, amines, etc., which because of their reactivity are difficult to store and transport and, furthermore, are toxic.

The preparation of 1,3,5-triazine carbamates is described for example in DE-A1 101 51 564 or WO 97/08235, p. 3 lines 9-22. The preparation routes specified therein lead to alkyl-substituted 1,3,5-triazine carbamates. The strongly basic reaction medium makes these methods unsuitable for functional groups such as ester or carbamate groups.

EP-A2 305 115 describes radiation-activable 1,3,5-triazine compounds which comprise at least one halogenated group $CX_3$ and via UV exposure are able photochemically to initiate a free-radical addition polymerization. The triazine compounds may further comprise free-radically polymerizable groups, e.g., hydroxyethyl acrylate, attached via a urethane group.

EP-A 359 430 likewise describes halogenated 1,3,5-triazine compounds which simultaneously comprise a free-radically polymerizable group. Compounds of this kind form free radicals under the influence of light.

The radiation-activable halogen groups in these systems have an adverse effect on the UV stability of compounds or coatings which comprise them, and lead to increased yellowing.

EP-A 366 884 describes 1,3,5-triazine compounds which comprise at least two vinyl-terminated groups and at least one carbamyl group. These 1,3,5-triazine compounds comprise reaction products of melamine with aldehydes, especially with formaldehyde. Besides the vinyl end groups, the 1,3,5-triazine compounds comprise methylol and/or alkylated methylol groups.

A similar system is described in EP-A 473 948. It comprises 1,3,5-triazines which are obtained by condensing melamine with formaldehyde and comprise ethylenically unsaturated groups. Groups of this kind are sensitive to acid.

It was an object of the present invention to provide a process for preparing 1,3,5-triazine carbamates and 1,3,5-triazine ureas which ought to start from compounds of low or zero toxicity and ought to yield the target products in high yields with short reaction times.

This object is achieved through a process for preparing 1,3,5-triazine carbamates of formula (I),

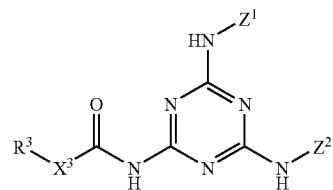

from 1,3,5-triazine carbamates of formula (II),

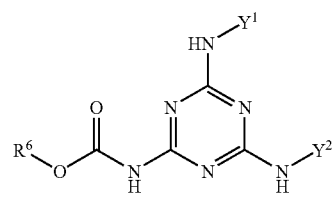

in which
either $Y^1$ and $Z^1$ are both hydrogen or $Y^1$ is a group of formula —(CO)—O—$R^4$ and $Z^1$ is a group of formula —(CO)—$X^1$—$R^1$,
either $Y^2$ and $Z^2$ are both hydrogen or $Y^2$ is a group of formula —(CO)—O—$R^5$ and $Z^2$ is a group of formula —(CO)—$X^2$—$R^2$,
$R^1$, $R^2$, $R^3$, $R^4$, $R^5$ and $R^6$ each independently of one another are the radical of an alcohol or amine and
$X^1$, $X^2$ and $X^3$ each independently of one another are oxygen or unsubstituted nitrogen (NH),
which comprises
conducting the reaction at a temperature of 40 to 120° C. and in the presence of at least one catalyst selected from the group comprising tin compounds, cesium salts, alkali metal (hydrogen)carbonates and tertiary amines.

The process of the invention yields 1,3,5-triazine carbamates and 1,3,5-triazine ureas in yields which are improved over those of the prior art, with a consequent improvement in particular in the space/time yield in the preparation. Through the increase in the temperature as compared with curing at room temperature, and through the process regime of the invention, conversion rates are achieved, and hence compounds are preparable, which would not be achievable by reaction at room temperature.

Since the temperature in the catalyzed process of the invention is lower than in the case of purely thermal preparation, more favorable color numbers can be obtained.

The radicals $R^4$, $R^5$ and $R^6$ are each independently of one another derived from alcohols $R^4OH$, $R^5OH$ and $R^6OH$ which have a boiling point at atmospheric pressure of 120° C. or less, preferably of 100° C. or less, more preferably of 80° C. or less and very preferably of 70° C. or less.

Examples of the radical $R^4$, $R^5$ and $R^6$ are each independently of one another $C_1$-$C_4$ alkyl, by which is meant in this text methyl, ethyl, iso-propyl, n-propyl, n-butyl, iso-butyl, sec-butyl and tert-butyl, preference being given to methyl, ethyl and n-butyl, greater preference to methyl and n-butyl, and especially methyl.

The radicals $R^4$, $R^5$ and $R^6$ can be identical or different; preferably they comprise not more than two different radicals.

Preferred compounds (II) are those in which at least one, more preferably two, of the radicals $Y^1$ and $Y^2$ is/are the group(s) —(CO)—O—$R^4$ and/or —(CO)—O—$R^5$. Preferred compounds (I) accordingly are those in which at least one, more preferably two, of the radicals $Z^1$ and $Z^2$ is/are the group(s) —(CO)—$X^1$—$R^1$ and/or —(CO)—$X^2$—$R^2$.

1,3,5-Triazine carbamates (II) used with very particular preference are 1,3,5-triazine (trimethyl)carbamates, 1,3,5-triazine (triethyl)carbamates, 1,3,5-triazine (tri-n-butyl)carbamates or mixed methyl/n-butyl 1,3,5-triazine carbamates.

The preparation of the 1,3,5-triazine carbamates used is not critical to the invention and may take place for example as described in DE-A1 101 51 564 or WO 97/08235, p. 3, lines 9-22.

The radicals $R^1$—$X^1$, $R^2$—$X^2$ and $R^3$—$X^3$ are derived from alcohols $R^1OH$, $R^2OH$ and $R^3OH$ and/or amines $R^1NH_2$, $R^2NH_2$ and $R^3NH_2$.

Particular preference in the process of the invention is given to those alcohols $R^1OH$, $R^2OH$ and $R^3OH$ and/or amines $R^1NH_2$, $R^2NH_2$ and $R^3NH_2$ whose lowest-boiling representative has a boiling point difference of at least 20° C., preferably at least 40° C. and more preferably at least 60° C., from the highest-boiling of the alcohols $R^4OH$, $R^5OH$ and $R^6OH$.

The radicals $R^1$, $R^2$ and $R^3$ can, for example, be $C_1$-$C_{18}$ alkyl, $C_2$-$C_{18}$ alkyl, interrupted if appropriate by one or more oxygen and/or sulfur atoms and/or by one or more substituted or unsubstituted imino groups, or can be $C_2$-$C_{18}$ alkenyl, $C_6$-$C_{12}$ aryl, $C_5$-$C_{12}$ cycloalkyl or a five- or six-membered heterocycle containing oxygen, nitrogen and/or sulfur atoms, it being possible for said radicals each to be substituted by aryl, alkyl, aryloxy, alkyloxy, heteroatoms and/or heterocycles

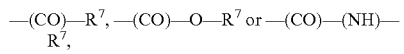

in which $R^7$ can be $C_1$-$C_{18}$ alkyl, $C_2$-$C_{18}$ alkyl, interrupted if appropriate by one or more oxygen and/or sulfur atoms and/or by one or more substituted or unsubstituted imino groups, or can be $C_2$-$C_{18}$ alkenyl, $C_6$-$C_{12}$ aryl, $C_5$-$C_{12}$ cycloalkyl or a five- or six-membered heterocycle containing oxygen, nitrogen and/or sulfur atoms, it being possible for said radicals each to be substituted by aryl, alkyl, aryloxy, alkyloxy, heteroatoms and/or heterocycles.

In these definitions $C_1$-$C_{18}$ alkyl and $C_2$-$C_{18}$ alkyl interrupted if appropriate by one or more oxygen and/or sulfur atoms and/or by one or more substituted or unsubstituted imino groups are for example $C_1$-$C_{18}$ alkyl optionally substituted by aryl, alkyl, aryloxy, alkyloxy, heteroatoms and/or heterocycles, examples of said optionally substituted $C_1$-$C_{18}$ alkyl being methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, or are $C_2$-$C_{18}$ alkyl interrupted if appropriate by one or more oxygen and/or sulfur atoms and/or by one or more substituted or unsubstituted imino groups, examples being 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-dioxatetradecyl.

There is no restriction on the number of oxygen and/or sulfur atoms and/or imino groups. In general the number is not more than 5 in the radical, preferably not more than 4 and very preferably not more than 3.

In addition there is generally at least one carbon atom, and preferably at least two, between two heteroatoms.

Examples of possible substituted or unsubstituted imino groups include imino, methyl-imino, iso-propylimino, n-butylimino and tert-butylimino.

Furthermore $C_2$-$C_{18}$ Alkenyl optionally substituted by aryl, alkyl, aryloxy, alkyloxy, heteroatoms and/or heterocycles is for example vinyl, 1-propenyl, allyl, methallyl, 1,1-dimethylallyl, 2-butenyl, 2-hexenyl, octenyl, undecenyl, dodecenyl, octadecenyl, 2-phenylvinyl, 2-methoxyvinyl, 2-ethoxyvinyl, 2-methoxyallyl, 3-methoxyallyl, 2-ethoxyallyl, 3-ethoxyallyl or 1- or 2-chlorovinyl, $C_6$-$C_{12}$ Aryl optionally substituted by aryl, alkyl, aryloxy, alkyloxy, heteroatoms and/or heterocycles is for example phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$ cycloalkyl optionally substituted by aryl, alkyl, aryloxy, alkyloxy, heteroatoms and/or heterocycles is for example cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or else a saturated or unsaturated bicyclic system such as norbornyl or norbornenyl, for example and
a five- or six-membered heterocycle containing oxygen, nitrogen and/or sulfur atoms is for example furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

In one embodiment of the invention the alcohols $R^1OH$, $R^2OH$ and $R^3OH$ can be monools, in other words alcohols having precisely one hydroxyl function (—OH).

Preferred monools $R^1OH$, $R^2OH$ and $R^3OH$ are n-butanol, sec-butanol, iso-butanol, tert-butanol, n-pentanol, n-hexanol, n-heptanol, n-octanol, n-decanol, 2-ethylhexanol, ethylene glycol monomethyl ether, ethylene glycol monoethyl ether, 1,3-propanediol monomethyl ether, lauryl alcohol (1-dodecanol), myristyl alcohol (1-tetradecanol), cetyl alcohol (1-hexadecanol), stearyl alcohol (1-octadecanol), 9-cis-octadecen-1-ol (oleyl alcohol), 9-trans-octadecen-1-ol, 9-cis-octadecene-1,12-diol (ricinoleyl alcohol), all-cis-9,12-octadecadien-1-ol (linoleyl alcohol), all-cis-9,12,15-octadecatrien-1-ol (linolenyl alcohol), 1-eicosanol (arachidyl alcohol), 9-cis-eicosen-1-ol (gadoleyl alcohol), 1-docosanol (behenyl alcohol), 1,3-cis-docosen-1-ol, 1,3-trans-docosen-1-ol (brassidyl alcohol), cyclopent-2-en-1-ol, cyclopent-3-en-1-ol, cyclohex-2-en-1-ol or allyl alcohol.

Additionally the alcohols in question may be alkoxylated monools of formula $$R^8O\text{—}[\text{—}X_i\text{—}]_n\text{—}H$$

in which
$R^8$ can be $C_1$-$C_{18}$ alkyl, preferably $C_1$-$C_4$ alkyl,
n is a positive integer between 1 and 50, preferably between 1 and 30, more preferably between 1 and 20 and very preferably between 2 and 10 and
each $X_i$ for i=1 to n can be selected independently of the others from the group consisting of —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—$CHVin$-O—, —$CHVin$-$CH_2$—O—, —$CH_2$—$CHPh$-O— and —$CHPh$-$CH_2$—O—, preferably from the group consisting of —$CH_2$—$CH_2$—O—, —$CH_2$—$CH(CH_3)$—O— and —$CH(CH_3)$—$CH_2$—O—, and more preferably —$CH_2$—$CH_2$—O—, in which Ph is phenyl and Vin is vinyl.

In one preferred embodiment of the present invention the monool is a compound which carries at least one, for example from one to three, preferably one or two and more preferably one polymerizable group and precisely one hydroxyl group.

Polymerizable groups are for example vinyl ether, acrylate or methacrylate groups, preferably (meth)acrylate groups and more preferably acrylate groups. Examples of compounds which carry at least one polymerizable group and precisely one hydroxyl group are those of formulae $$H_2C=CR^9\text{—}CO\text{—}O\text{—}R^{10}\text{—}OH, \quad (III)$$

$$H_2C=CR^9\text{—}CO\text{—}O\text{—}[\text{—}X_i\text{—}]_k\text{—}H \text{ or} \quad (IV)$$

$$H_2C=CH\text{—}O\text{—}R^{10}\text{—}OH, \quad (V)$$

in which
$R^9$ is hydrogen or methyl, preferably hydrogen,
$R^{10}$ is a divalent linear or branched $C_2$-$C_{18}$, preferably $C_2$-$C_{12}$, more preferably $C_2$-$C_8$ and very preferably $C_2$-$C_6$ alkylene radical, $X_i$ has the same definition as set out above and
k is a positive integer from 1 to 20, preferably from 2 to 15, more preferably from 2 to 10 and very preferably from 2 to 5.

Examples of $R^{10}$ are 1,2-ethylene, 1,2- or 1,3-propylene, 1,2-, 1,3- or 1,4-butylene, 1,6-hexylene, 1,1-dimethyl-1,2-ethylene, 1,2-dimethyl-1,2-ethylene, phenylethylene, preferably 1,2-ethylene, 1,2- or 1,3-propylene, 1,4-butylene or 1,6-hexylene, more preferably 1,2-ethylene, 1,2-propylene or 1,4-butylene and very preferably 1,2-ethylene.

Preferred compounds which carry at least one polymerizable group and precisely one hydroxyl group are hydroxyethyl (meth)acrylate, hydroxypropyl (meth)acrylate, 4-hydroxybutyl (meth)acrylate, 6-hydroxyhexyl (meth)acrylate, (meth)acrylic acid ethoxylated from two to ten times, preferably two to five times, and pentaerythrityl tri(meth)acrylate.

In one further embodiment of the invention the alcohols $R^1OH$, $R^2OH$ and $R^3OH$ can be diols or polyols, in other words alcohols having two or more than two hydroxyl functions (—OH), preferably 2 to 6, more preferably 2 to 4, very preferably 2 or 3 and in particular 2.

Examples of diols or polyols are 1,2-propanediol, ethylene glycol, diethylene glycol, triethylene glycol, tetraethylene glycol, pentaethylene glycol, 2,2-dimethyl-1,2-ethanediol, 1,3-propanediol, 1,2-butanediol, 1,3-butanediol, 1,4-butanediol, but-2-ene-1,4-diol, but-2-yne-1,4-diol, tricyclodecanedimethanol, trimethylolbutane, trimethylolpropane, trimethylolethane, neopentyl glycol, neopentyl glycol hydroxypivalate, pentaerythritol, 2-ethyl-1,3-propanediol, 2-methyl-1,3-propanediol, 2-ethyl-1,3-hexanediol, 2,4-diethyloctane-1,3-diol, glycerol, ditrimethylolpropane, dipentaerythritol, hydroquinone, bisphenol A, bisphenol F, bisphenol B, bisphenol S, 2,2-bis(4-hydroxycyclohexyl)propane, 1,1-, 1,2-, 1,3- and 1,4-cyclohexanedimethanol, 1,2-, 1,3- or 1,4-cyclohexanediol, sorbitol, mannitol, diglycerol, threitol, erythritol, adonitol (ribitol), arabitol (lyxitol), xylitol, dulcitol (galactitol), maltitol, isomalt, 1,2-, 1,3- or 1,4-aminophenol, 1,2-, 1,3- or 1,4-bishydroxymethylbenzene, 2-, 3- or 4-hydroxybenzoic acid, 2-, 3- or 4-amino-benzoic acid, each of which may if appropriate be alkoxylated, preferably ethoxylated and/or propoxylated and more preferably ethoxylated, polyTHF having a molar mass between 162 and 2000, poly-1,3-propanediol having a molar mass between 134 and 1178 or polyethylene glycol having a molar mass between 106 and 1000.

In one particular embodiment it is also possible for at least one of the alcohols $R^1OH$, $R^2OH$ and $R^3OH$ to be selected from polyetherols or polyesterols with the proviso that at the same time at least one of the alcohols $R^1OH$, $R^2OH$ and $R^3OH$ is one of the above-recited monools having at least one polymerizable and precisely one hydroxyl group.

Examples of suitable polyesterols are those as may be prepared by esterifying polycarboxylic acids, preferably dicarboxylic acids, with the abovementioned polyols.

The starting materials for such polyesterols are known to the skilled worker. With preference it is possible to use as polycarboxylic acids oxalic acid, maleic acid, fumaric acid, succinic acid, glutaric acid, adipic acid, sebacic acid, dodecanedioic acid, o-phthalic acid, isophthalic acid, terephthalic acid, trimellitic acid, azelaic acid, 1,4-cyclohexanedicarboxylic acid or tetrahydrophthalic acid, their isomers and hydrogenation products and also esterifiable derivatives, such as anhydrides or dialkyl esters, $C_1$-$C_4$ alkyl esters for example, preferably methyl, ethyl or n-butyl esters, of said acids.

Suitable hydroxy-bearing carboxylic acids or lactones include 4-hydroxybenzoic acid, 6-hydroxy-2-naphthoic acid, pivalolactone and ε-caprolactone. Suitable polyols include the abovementioned polyfunctional alcohols, preferably neopentyl glycol, trimethylolpropane, trimethylolethane, pentaerythritol, dimethylolpropionic acid or dimethylolbutyric acid.

The preferred molecular weight of the polyesterols is up to 5000 g/mol, more preferably up to 3000, very preferably 500 to 2000 and in particular 500 to 1500 g/mol.

In a further embodiment of the invention the amines $R^1NH_2$, $R^2NH_2$ and $R^3NH_2$ can be monoamines, in other words amines having precisely one amino function (—$NH_2$).

These amines may be, for example, methylamine, ethylamine, iso-propylamine, n-propylamine, n-butylamine, iso-butylamine, sec-butylamine, tert-butylamine, n-pentylamine, n-hexylamine, n-heptylamine, n-octylamine, n-decylamine, n-dodecylamine, 2-ethylhexylamine, stearylamine, cetylamine or laurylamine, and also cyclopentylamine, cyclohexylamine, cyclooctylamine, cyclododecylamine, monoethanolamine, 1,2-propanolamine, 1,3-propanolamine, 1,4-butanolamine, 1,6-hexanolamine and aminoethylethanolamine.

The reaction is preferably conducted in the presence of at least one monoamine, monool or mixtures of at least one monool and at least one polyol, more preferably in the presence of at least one monool or mixtures of at least one monool and at least one polyol, and very preferably in the presence of precisely one monool or a mixture of precisely one monool and precisely one polyol.

The catalyst used in the reaction, in accordance with the invention, is selected from the group comprising tin compounds, cesium salts, alkali metal (hydrogen)carbonates and tertiary amines.

Tin compounds are all organometallic tin compounds, preferably tin(II) n-octanoate, tin(II) 2-ethyl-I-hexanoate, tin (II) laurate, dibutyltin oxide, dibutyltin dichloride, dibutyltin diacetate, dibutyltin dilaurate, dibutyltin dimaleate or dioctyltin diacetate, more preferably tin(II) n-octanoate, tin(II) 2-ethyl-I-hexanoate, tin(II) laurate, dibutyltin oxide, dibutyltin diacetate or dibutyltin dilaurate, very preferably dibutyltin oxide, dibutyltin diacetate or dibutyltin dilaurate and especially dibutyltin dilaurate.

Tin compounds, however, are toxicologically objectionable and are therefore less preferred in accordance with the invention, particularly when they remain in the reaction mixture. Contrastingly cesium salts and alkali metal (hydrogen) carbonates are unobjectionable.

Preferred cesium salts are those containing the following anions: $F^-$, $Cl^-$, $ClO^-$, $ClO_3^-$, $ClO_4^-$, $Br^-$, $I^-$, $IO_3^-$, $CN^-$, $OCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, $(OC_mH_{2m+1})^-$, $(C_mHO_{2m-1}O_2)^-$, $(C_mHO_{2m-3}O_2)^-$ and $(C_{m+1}H_{2m-2}O_4)^{2-}$, m standing for the numbers 1 to 20.

Particular preference is given to cesium carboxylates where the anion conforms to formulae $(C_mH_{2m-1}O_2)^-$ and $(C_{m+1}H_{2m-2}O_4)^{2-}$ with m being 1 to 20. Especially preferred cesium salts have monocarboxylate anions of general formula $(C_mH_{2m-1}O_2)^-$, m being from 1 to 20. Particular mention may be made in this context of formate, acetate, propionate, hexanoate and 2-ethylhexanoate, with very particular preference being given to cesium acetate.

The cesium salts can be added to the batch in solid form or in dissolved form. Suitable solvents are polar aprotic solvents or else protic solvents. Particularly suitable solvents besides water are alcohols; very particular suitability is possessed by polyols, such as ethanediols, propanediols or butanediols, and glycol ethers, for example.

In order to improve the solubility of the cesium salts in the reaction medium they can be used if appropriate with phase transfer catalysts. Suitable phase transfer catalysts are, for example, crown ethers such as 18-crown-6 or tetraalkylammonium salts such as tetrabutylammonium bromide.

Alkali metal (hydrogen)carbonates are for example the carbonates $Li_2CO_3$, $Na_2CO_3$ and $K_2CO_3$ and also the hydrogencarbonates $LiHCO_3$, $NaHCO_3$ and $KHCO_3$, preference being given to $Na_2CO_3$ and $K_2CO_3$ and particular preference to $K_2CO_3$.

Tertiary amines are for example trioctylamine, tridodecylamine, tribenzylamine, N,N,N',N'-tetramethylethylenediamine, 1-methylpyrrole, pyridine, 4-dimethylaminopyridine, picoline, N,N'-dimethylpiperazine, N-methylmorpholine, N-methylpiperidine, N-ethylpiperidine, N,N-dimethylaniline, N,N-dimethylbenzylamine, N-methylimidazole, 1,4-diazabicyclo[2.2.2]octane, 1,5-diazabicyclo[4.3.0]non-5-ene or 1,8-diaza-bicyclo[5.4.0]undec-7-ene.

Preferred catalysts are cesium salts and alkali metal (hydrogen)carbonates, particular preference being given to the cesium salts.

Catalysts that might further be contemplated include alkoxides (examples being sodium or potassium alkoxides of $C_1$-$C_4$ alkyl alcohols, preferably sodium and potassium methoxide and ethoxide), hydroxides (NaOH, KOH, $Ca(OH)_2$, for example), carboxylates (examples being sodium or potassium salts of $C_1$-$C_4$ alkylcarboxylic acids or $ClCH_2COONa$), oxides (CaO, MgO, ZnO, $Tl_2O_3$, PbO, for example), phosphines ($PPh_3$ for example), zinc salts ($ZnCl_2$) and ion exchangers (strongly or weakly alkaline anion exchangers, such as DOWEX® MSA-1).

The catalyst is used usually in amounts from 0.001 to 0.3 mol %, preferably 0.005 to 0.25 mol %, more preferably 0.01 to 0.2 mol % and very preferably 0.02 to 0.1 mol %, based on the starting compound (II).

The reaction is carried out in accordance with the invention at a temperature of at least 40° C., preferably at least 50° C., more preferably at least 60° C. and very preferably at least 70° C.

The reaction temperature is preferably above the boiling temperature of the alcohol that is to be separated off.

In accordance with the invention the upper temperature limit is generally not more than 120° C., in particular not more than 110° C.

An uncatalyzed reaction generally needs at least 110° C. in order to bring acceptable conversion rates; good conversion rates are generally only obtained above 120 to 130° C. As a result of such high temperatures, however, the resulting product is frequently colored. Particularly sensitive substrates, such as polymerizable monools or polyols for example, tend to thermal polymerization at temperatures above 130° C. and were therefore not preparable with the thermal reactions known from the prior art.

Thus the process of the invention can be employed with advantage for preparing 1,3,5-triazine carbamates and 1,3,5-triazine ureas containing at least one polymerizable group.

Where polymerizable compounds are used the reaction can be conducted preferably in the presence of free-radical stabilizers. Suitable free-radical stabilizers are known to the skilled worker, preferably 4-methoxyphenol (100-4000 ppm), 2,6-di-t-butylhydro-quinone (50-1000 ppm), phenothiazine (10-500 ppm) or triphenyl phosphite (50-1000 ppm).

An advantage of the inventive reaction is that by adding the catalyst of the invention with the same or a shortened reaction time and at least equal conversion rates under otherwise identical conditions the reaction temperature can be lowered by at least 10° C., preferably at least 15° C. and more preferably at least 20° C. as compared with the uncatalyzed reaction.

The reaction time varies according to substrate and can be from 15 minutes to 12 hours, preferably 30 minutes to 10 hours, more preferably 45 minutes to 8 hours and very preferably 1 to 7 hours.

The stoichiometry with respect to alcohol $R^1OH$, $R^2OH$ and $R^3OH$ and/or amine $R^1NH_2$, $R^2NH_2$ and $R^3NH_2$ employed, in relation to carbamate groups to be converted is generally 0.5-1.5:1 mol/mol, preferably 0.7-1.3:1, more preferably 0.8 to 1.2:1, very preferably 0.8-1.1:1, in particular 0.9-1:1, and especially 0.95-1.0:1 mol/mol.

The reaction can take place in bulk or in a suitable solvent, i.e., a solvent that does not react with a 1,3,5-triazine carbamate or 1,3,5-triazine urea. Examples of possible such solvents include acetone, acetylacetone, acetoacetic esters, ethyl acetate, butyl acetate, ethylene glycol dimethyl ether, ethylene glycol diethyl ether, ethylene glycol di-n-butyl ether, diethylene glycol dimethyl ether, diethylene glycol diethyl ether, diethylene glycol di-n-butyl ether, $C_1$-$C_4$ alkylene carbonates, especially ethylene carbonate, 1,2- or 1,3-propylene carbonate, THF, dioxane, dimethylformamide, dimethyl sulfoxide, N-methylpyrrolidone, 1,3-dioxolane, iso-butyl methyl ketone, ethyl methyl ketone, diethyl ether, tert-butyl methyl ether, tert-butyl ethyl ether, n-pentane, n-hexane, n-heptane, cyclohexane, methylcyclohexane, benzene, toluene, xylene, paraffins, naphtha, mineral oil or petroleum ether fractions.

Preferably the reaction is conducted in bulk.

The conversion rates achieved with the process of the invention are generally at least 40%, preferably at least 50%, more preferably at least 70% and very preferably at least 80%.

The reaction can be conducted in a gas or gas mixture which is inert under the reaction conditions, examples being gas mixtures with an oxygen content below 10%, preferably below 8% and more preferably below 7% by volume, preference being given to nitrogen, argon, helium, nitrogen/noble gas mixtures, carbon dioxide or carbon monoxide, and particular preference to nitrogen.

In one preferred embodiment of the process of the invention the liberated lower alcohols $R^4OH$, $R^5OH$ and $R^6OH$ are separated off appropriately so as to shift the reaction equilibrium in favor of the product.

The lower alcohol $R^4OH$, $R^5OH$ or $R^6OH$ can be separated off for example by distillation, stripping, reduced pressure, azeotropic removal, absorption, pervaporation and diffusion via membranes.

Preference is given to distillative removal, if appropriate under reduced pressure, which if appropriate can be assisted by stripping with a gas which is inert under the reaction conditions.

For stripping, a gas mixture or gas which is inert under the reaction conditions is passed through the reaction mixture, by being bubbled in, for example.

Absorption can take place for example with molecular sieves (pore size in the region, for example, of about 3-10 angstroms). Diffusion can take place, for example, by means of suitable semipermeable membranes.

The reaction can take place in accordance with the invention continuously, batchwise or semibatchwise, preferably batchwise or semibatchwise.

For that purpose in general the starting material of formula (II) is introduced as an initial charge and brought to the desired reaction temperature.

Before or after the desired reaction temperature has been reached, the catalyst can be added at least in part and the alcohol/amine $R^1XH$, $R^2XH$, $R^3XH$ can be added in full, in portions or continuously. If the catalyst has not yet been added in full it too may be added subsequently in portions.

It can be advantageous to raise the reaction temperature in the course of the reaction, by at least 10° C. for example, preferably by at least 15° C. and more preferably by at least 20° C. in relation to the temperature at the start of the reaction.

The course of the reaction can be monitored, for example, by monitoring the amount of liberated alcohol $R^4OH$, $R^5OH$ or $R^6OH$ and terminating the reaction when the desired conversion rate has been achieved.

The reaction can be stopped, for example, by cooling down or by direct cooling with a solvent.

The reaction is preferably carried out in a backmixed reaction tank in which mixing can be accomplished for example by stirring, introduction through nozzles or a pumped circulation.

The temperature adjustment can either be via the reactor walls or by means of a heat exchanger in the pumped circulation.

If the liberated lower alcohol $R^4OH$, $R^5OH$ or $R^6OH$ is separated off by distillation and/or stripping, then the reactor may be surmounted by a packed column or tray column, for which 2 to 10 theoretical plates are generally sufficient.

Separation of the lower alcohol can be assisted by applying a slight vacuum: for example, the reaction can be carried out at a pressure of from 200 hPa to atmospheric pressure, preferably 300 hPa to atmospheric pressure, more preferably 500 hPa to atmospheric pressure, very preferably at 800 hPa to atmospheric pressure, and in particular at atmospheric pressure.

After the end of the reaction the reaction mixture may additionally be subjected to washing and/or decoloring.

For washing, the reaction mixture is treated in a washer with a washing fluid, an example being water or a 5-30%, preferably 5-20%, more preferably 5-15% strength by weight solution of sodium chloride, potassium chloride, ammonium chloride, sodium sulfate or ammonium sulfate, preferably water or sodium chloride solution.

Washing can be carried out, for example, in a stirred vessel or in other conventional apparatus, e.g., in a column or mixer-settler apparatus.

The reaction mixture can if necessary be subjected to decoloring, by treatment for example with activated carbon or metal oxides, such as alumina, silicon oxide, magnesium oxide, zirconium oxide, boron oxide or mixtures thereof, in amounts for example of 0.1-50% by weight, preferably 0.5 to 25% by weight, more preferably 1-10% by weight, and at temperatures of for example 10 to 100° C., preferably 20 to 80° C. and more preferably 30 to 60° C.

This can take place by adding the pulverulent or granular decolorizer to the reaction mixture with subsequent filtration, or by passing the reaction mixture over a bed of the decolorizer in the form of any desired suitable shaped bodies.

An advantage of the present invention is that, as a result of the catalyzed process regime of the invention, fewer of the carbamate groups —$COOR^4$, —$COOR^5$ and/or —$COOR^6$ present in the starting product are hydrolyzed than in the case of the purely thermal process regime, and hence when using 1,3,5-triazine triscarbamates as starting products in the catalyzed process regime of the invention the fraction of 2-amino-1,3,5-triazine 4,6-biscarbamates obtained is lower than in the case of the thermal, uncatalyzed reaction regime. These 2-amino-1,3,5-triazine 4,6-biscarbamates tend toward crystallization, and hence lead to instances of precipitation in the product, and can lead to optical defects if the products thus contaminated are used in a paint coating.

The 1,3,5-triazine carbamates prepared according to the process of the invention can be used for coating a variety of substrates such as wood, wood veneer, paper, paper board, cardboard, textile, leather, nonwoven fabric, plastics surfaces, glass, ceramics, mineral building materials and coated or uncoated metals.

Where they are used in coating compositions the 1,3,5-triazine carbamates prepared in accordance with the invention can be employed in particular in primers, surfacers, pigmented topcoat and clearcoat materials in the sector of automotive refinish or large-vehicle finishing. Coating compositions of this kind are particularly suitable for applications which call for particularly high application reliability, exterior weathering stability, optical qualities, solvent resistance, chemical resistance and water resistance, such as in automotive refinish and large-vehicle finishing.

The coatings may be cured thermally and/or—if they comprise free-radically polymerizable groups—by actinic radiation.

Curing of the coating by actinic radiation may necessitate the use of a photoinitiator.

For the thermal curing of the coatings polyol components are added to the formulation so that crosslinking ensues.

ppm and percentage figures used in this specification are by weight unless otherwise indicated.

The examples which follow are intended to illustrate the invention, but not to restrict it to these examples.

EXAMPLES

Comparative Example 1

1 g of 2,4,6-tris(methylcarbamoyl)-1,3,5-triazine was dissolved in 100 ml of n-butanol and the solution was stirred at 110° C.

Conversion after 280 minutes: 78% 2,4,6-tris(butylcarbamoyl)-1,3,5-triazine. The 2,4,6-tris(butylcarbamoyl)-1,3,5-triazine conversion was determined via HPLC.

Example 1

A 250-ml four-necked reaction flask equipped with distillation bridge, Liebig condenser and stirrer was charged with 40.5 g of n-butanol, and 0.5 ml of butanolic cesium acetate solution (2.5 mg/l) was metered in.

After the internal temperature of 110° C. had been reached, 2.50 g of 2,4,6-tris(methyl-carbamoyl)-1,3,5-triazine was stirred in and dissolved.

The methanol formed was removed by distillation.

Conversion rate after 280 minutes: 85% 2,4,6-tris(butylcarbamoyl)-1,3,5-triazine (HPLC).

Comparative Example 2

In a 250 ml four-necked reaction flask equipped with distillation bridge, Liebig condenser and stirrer 6.0 g of 2,4,6-tris(methylcarbamoyl)-1,3,5-triazine, 6.97 g of 2-hydroxyethyl acrylate, 12.5 mg of 4-methoxyphenol, 4 mg of 2,6-di-t-butyl-p-cresol and 0.3 mg of phenothiazine were dissolved in 4.74 g of n-butyl acetate and the solution was brought to an internal temperature of 110° C. The methanol formed was removed by distillation.

Conversion rate after 300 minutes: 25% of the 2-hydroxyethyl acrylate, 4% 2,4,6-tris(2-ethoxyacrylatocarbamoyl)-1,3,5-triazine (HPLC).

Example 2

In a 250 ml four-necked reaction flask equipped with distillation bridge, Liebig condenser and stirrer 6.0 g of 2,4,6-tris(methylcarbamoyl)-1,3,5-triazine, 6.97 g of 2-hydroxyethyl acrylate, 12.5 mg of 4-methoxyphenol, 4 mg of 2,6-di-t-butyl-p-cresol and 0.3 mg of phenothiazine and also 0.96 mg of cesium acetate were dissolved in 12.32 g of n-butyl acetate and the solution was brought to an internal temperature of 110° C. The methanol formed was removed by distillation.

Conversion rate after 300 minutes: 50% of the 2-hydroxyethyl acrylate, 17% 2,4,6-tris-(2-ethoxyacrylatocarbamoyl)-1,3,5-triazine (HPLC).

Examples 3-10

A suspension of 0.1369 of p-methoxyphenol, 0.045 g of di-tert-butyl-p-kresol, 0.003 g of phenothiazine, 0.016 g of dibutyltin dilaurate (DBTL), 2,4,6-trisalkoxycarbamoyl-1,3,5-triazine, diol and/or polyesterol and also hydroxyethyl acrylate (HEA), as indicated in the table, in 30.0 ml of methyl isobutyl ketone (MIBK) was stirred at a bath temperature of 112° C. for 4 hours. Subsequently the reaction mixture was distilled at a bath temperature of 52° C. under a reduced pressure of 750 mbar for 2 hours. This gave a clear resin solution. The molar amounts employed are given in the table.

Film Tests

The resin solutions were adjusted by adding methyl isobutyl ketone to a viscosity of about 3.5 Pas and were mixed with 4 percent by weight (based on the solids content) of 2-hydroxy-2-methyl-1-phenylpropan-1-one as photoinitiator (Darocur® 1173 from Ciba Spezialitätenchemie). The coating materials were applied using a box-type doctor blade to the respective substrate and dried at 60° C. for 30 minutes to remove the solvent.

The coatings were cured thermally by 30 minutes' heat treatment or exposed under an undoped high-pressure mercury lamp (output 120 W/cm) with a lamp-to-substrate distance of 12 cm and a belt speed of 10 m/min approximately at a temperature of 100° C., or were first exposed and then cured thermally.

The pendulum hardness (PD) was determined in accordance with DIN 53157 and is a measure of the hardness of the coating. The result is reported in seconds until the pendulum comes to a standstill (s). High values in this test denote high hardness. The films for determining the pendulum hardness were applied to glass using a box-type doctor blade. The film thickness prior to curing was 100 μm.

The Erichsen cupping (EC) was determined in accordance with DIN 53156 and is a measure of the flexibility and elasticity. The result is reported in millimeters (mm). High values in this test denote high flexibility. The films for determining the Erichsen cupping were applied to sheet metal using a wire-wound doctor blade. The film thickness prior to curing was 50 μm.

TABLE 1

| Example | 2,4,6-Tris(alkoxy-carbamoyl)-1,3,5-triazine (mol) | HEA (mol) | Diol (mol) | Curing | PD (s) | EC (mm) |
|---|---|---|---|---|---|---|
| 3 | 0.4 [1] | 1.2 | 0.2 A | therm. | 8 | 9.8 |
|   |         |     |        | photochem. | 10 | 9.9 |
|   |         |     |        | photochem. + therm. | 39 | 9.8 |
| 4 | 0.2 [1] | 0.6 | 0.05 A | therm. | 17 | 9.8 |
|   |         |     |        | photochem. | 21 | 9.8 |
|   |         |     |        | photochem. + therm. | 76 | 9.4 |
| 5 | 0.1 [1] | 0.6 | 0.025 A | therm. | 54 | 9.7 |
|   |         |     |        | photochem. | 36 | 7.2 |
|   |         |     |        | photochem. + therm. | 170 | 7.3 |
| 6 | 0.1 [2] | 0.3 | —       | therm. | 46 | 5.1 |
|   |         |     |        | photochem. | 200 | 1.2 |
|   |         |     |        | photochem. + therm. | 235 | 2.1 |
| 7 | 0.1 [2] | 0.3 | 0.125 A | therm. | 60 | 9.8 |
|   |         |     |        | photochem. | 83 | 6.1 |
|   |         |     |        | photochem. + therm. | 182 | 1.1 |
| 8 | 0.4 [2] | 1.2 | 0.008 A | therm. | 126 | 5.1 |
|   |         |     |        | photochem. | 153 | 1.1 |
|   |         |     |        | photochem. + therm. | 235 | 3.8 |
| 9 | 0.4 [2] | 1.2 | 0.2 B   | therm. | 221 | 3.5 |
|   |         |     |        | photochem. | 161 | 2.3 |
|   |         |     |        | photochem. + therm. | 242 | 2.1 |
| 10 | 0.1 [2] | 0.3 | 6.7 A  | therm. | 66 | 4.5 |
|    |         |     | 0.0067 B | photochem. | 129 | 1.1 |
|    |         |     |        | photochem. + therm. | 210 | 1.1 |

[1] 2,4,6-Tris(methoxycarbamoyl)-1,3,5-triazine
[2] 2,4,6-Tris(methoxy/butoxy-carbamoyl)-1,3,5-triazine (molar methyl:butyl ratio = 60:40)
A Polyester formed from 1 mol of adipic acid, 1 mol of isophthalic acid, and 2 mol of 1,6-hexanediol, molar mass about 1000 g/mol
B 1,4-Butanediol The examples show that complete curing is achieved only by combining thermal with photochemical crosslinking. In this way, with the compounds of the invention, extraordinarily hard coatings are obtained.

We claim:

1. A process for preparing a 1,3,5-triazine carbamate of the formula (I):

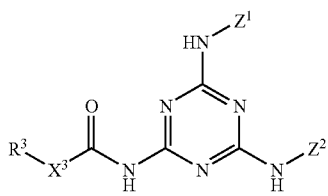

wherein
   $Z^1$ is hydrogen or a group of formula —(CO)—O—$R^1$,
   $Z^2$ is hydrogen or a group of formula —(CO)—O—$R^2$,
   $X^3$ is oxygen, and
   $R^1$ is the radical of an alcohol represented by the formula $R^1$OH,
   $R^2$ is the radical of the alcohol represented by the formula $R^2$OH,
   $R^3$ is the radical of an alcohol represented by the formula $R^3$OH, from an 1,3,5-triazine carbamate of the formula (II):

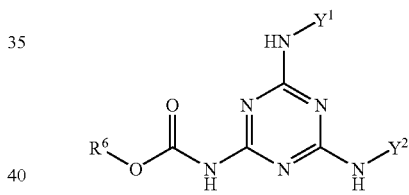

wherein
   $Y^1$ is hydrogen or a group of formula —(CO)—O—$R^4$,
   $Y^2$ is hydrogen or a group of formula —(CO)—O—$R^5$ and,
   $R^4$ is the radical of the alcohol represented by the formula $R^4$OH,
   $R^5$ is the radical of the alcohol represented by the formula $R^5$OH,
   $R^6$ is the radical of the alcohol represented by the formula $R^6$OH,
   wherein $R^4$, $R^5$ and $R^6$ are, independently, $C_{1-4}$ alkyl,
wherein
   (1) if $Z^1$ is hydrogen then $Y^1$ is hydrogen,
   (2) if $Z^1$ is a group of formula —(CO)—O—$R^1$ then $Y^1$ is a group of formula —(CO)—O—$R^4$,
   (3) if $Z^2$ is hydrogen then $Y^2$ is hydrogen, and
   (4) if $Z^2$ is a group of formula —(CO)—O—$R^2$ then $Y^2$ is a group of formula —(CO)—O—$R^5$, consisting of:
   reacting the 1,3,5-triazine carbamate of formula (II) at a temperature of 40 to 120° C. with an alcohol of the formula $R^3$—OH and, optionally, with an alcohol of the formula $R^2$—OH and/or $R^1$OH to produce the 1,3,5-triazine carbamate of the formula (I) and an alcohol of the formula $R^6$OH and optionally an alcohol of the formula $R^4$OH if $Y^1$ is a group of formula —(CO)—O—$R^4$ and/or an alcohol of the formula $R^5$OH if $Y^2$ is a group of formula —(CO)—O—$R^5$, in the presence of at least one catalyst selected from the group consisting of tin compounds, cesium salts, alkali metal (hydrogen)carbonates and tertiary amines, optionally in the presence of a solvent that does not react with the 1,3,5-triazine carbamate, optionally under a gas or gas mixture which is inert under the reaction conditions, wherein the alcohols $R^1OH$, $R^2OH$ and $R^3OH$ are, independently, selected from the group consisting of n-butanol, sec-butanol, iso-butanol, tert-butanol, n-pentanol, n-hexanol, n-heptanol, n-octanol, n-decanol, 2-ethylhexanol, ethylene glycol monomethyl ether, ethylene glycol monoethyl ether, 1,3-propanediol monomethyl ether, lauryl alcohol (1-dodecanol), myristyl alcohol (1-tetradecanol), cetyl alcohol (1-hexadecanol), stearyl alcohol (1-octadecanol), 9-cis-octadecen-1-ol (oleyl alcohol), 9-trans-octadecen-1-ol, 9-cis-octadecene-1, 12-diol (ricinoleyl alcohol), all-cis-9,12-octadecadien-1-ol (linoleyl alcohol), all-cis-9,12,15-octadecatrien-1-ol (linolenyl alcohol), 1-eicosanol (arachidyl alcohol), 9-cis-eicosen-1-ol (gadoleyl alcohol), 1-docosanol (behenyl alcohol), 1,3-cis-docosen-1-ol, 1,3-trans-docosen-1-ol (brassidyl alcohol), cyclopent-2-en-1-ol, cyclopent-3-en-1-ol, cyclohex-2-en-1-ol, allyl alcohol, an alkoxylated monool of formula:

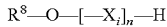

wherein $R^8$ is $C_1$-$C_{18}$ alkyl, n is a positive integer between 1 and 50 and each $X_i$ for i=1 to n can be selected independently of the others from the group consisting of —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O— and —CHPh-$CH_2$—O—, in which Ph is phenyl and Vin is vinyl, a monool which carries at least one polymerizable group and one hydroxyl group, the monool is represented by the formula:

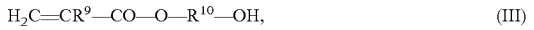

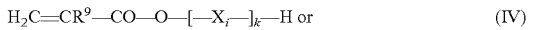

wherein $R^9$ is hydrogen or methyl, $R^{10}$ is a divalent linear or branched $C_2$-$C_{18}$ alkylene radical, $X_i$ is —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O— and —CHPh-$CH_2$—O—, in which Ph is phenyl and Vin is vinyl, and k is a positive integer from 1 to 20, and a polyetherol or polyesterol containing at least one polymerizable group and one hydroxyl group.

2. The process of claim 1, wherein $Z^1$ and $Y^1$ are hydrogen.

3. The process of claim 1, wherein $Z^1$ is a group of formula —(CO)—O—$R^1$ and $Y^1$ is a group of formula —(CO)—O—$R^4$.

4. The process of claim 1, wherein $Z^2$ and $Y^2$ are hydrogen.

5. The process of claim 1, wherein $Z^2$ is a group of formula —(CO)—O—$R^2$ and $Y^2$ is a group of formula —(CO)—O—$R^5$.

6. The process of claim 1, wherein $Y^1$ is a group of formula —(CO)—O—$R^4$ and $Y^2$ is a group of formula —(CO)—O—$R^5$.

7. The process of claim 1, wherein the alcohol $R^3OH$ is an alkoxylated monool of formula:

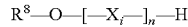

wherein $R^8$ is $C_1$-$C_{18}$ alkyl, n is a positive integer between 1 and 50 and each $X_i$ for i=1 to n can be selected independently of the others from the group consisting of —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHPh-O— and —CHPh-$CH_2$—O—, in which Ph is phenyl and Vin is vinyl.

8. The process of claim 1, wherein the alcohol $R^3OH$ is a monool which carries at least one polymerizable group and one hydroxyl group.

9. The process according to claim 1, wherein the alcohol $R^3OH$ is a monool is represented by the formula:

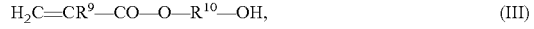

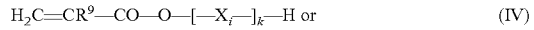

wherein $R^9$ is hydrogen or methyl, $R^{10}$ is a divalent linear or branched $C_2$-$C_{18}$ alkylene radical, $X_i$ is —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHPh-O— and —CHPh-$CH_2$—O—, in which Ph is phenyl and Vin is vinyl, and k is a positive integer from 1 to 20.

10. The process of claim 1, wherein the alcohol $R^3OH$ is a polyetherol or polyesterol containing at least one polymerizable group and one hydroxyl group.

11. The process of claim 1, wherein the alcohols $R^6OH$ and optionally $R^4OH$ and/or $R^5OH$ are separated by distillation from the reaction mixture.

12. The process of claim 1, wherein the catalyst comprises a tin compound.

13. The process of claim 1, wherein the catalyst comprises a cesium salt.

14. The process of claim 1, wherein the catalyst comprises an alkali metal (hydrogen)carbonate.

15. The process according to claim 1, wherein the catalyst comprises a tertiary amine, wherein the alcohol $R^3OH$ is alkoxylated monool of formula:

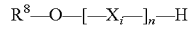

wherein $R^8$ can be $C_1$-$C_{18}$ alkyl, n is a positive integer between 1 and 50 and each $X_i$ for i=1 to n can be selected independently of the others from the group consisting of —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O— and —CHPh-$CH_2$—O—, in which Ph is phenyl and Vin is vinyl, or wherein the alcohol is a monool and represented by the formula:

$$H_2C=CR^9-CO-O-[-X_i-]_k-H \text{ or} \qquad (IV)$$

$$H_2C=CH-O-R^{10}-OH \qquad (V)$$

wherein $R^9$ is hydrogen or methyl, $R^{10}$ is a divalent linear or branched $C_2$-$C_{18}$ alkylene radical, $X_i$ is —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O— and —CHPh-$CH_2$—O—, in which Ph is phenyl and Vin is vinyl, and k is a positive integer from 1 to 20.

16. The process according to claim 1, wherein polymerizable compounds are used in the presence of at least one free radical stabilizer.

17. The process according to claim 16, wherein the free radical stabilizer comprises at least one member selected from the group consisting of 4-methoxyphenol, 2,6-di-t-butylhydro-quinone, phenothiazine or triphenyl phosphite.

18. The process according to claim 12, wherein the alcohol $R^4OH$, $R^5OH$ or $R^6OH$ is separated off by distillation, stripping, reduced pressure, azeotropic removal, absorption, pervaporation or diffusion via membranes.

19. The process according to claim 1, which is conducted in the presence of the solvent that does not react with the 1,3,5-triazine carbamate.

20. The process according to claim 19, wherein the solvent comprises at least one member selected from the group consisting of acetone, acetylacetone, acetoacetic esters, ethyl acetate, butyl acetate, ethylene glycol dimethyl ether, ethylene glycol diethyl ether, ethylene glycol di-n-butyl ether, diethylene glycol dimethyl ether, diethylene glycol diethyl ether, diethylene glycol di-n-butyl ether, $C_1$-$C_4$ alkylene carbonates, THF, dioxane, dimethylformamide, dimethyl sulfoxide, N-methylpyrrolidone, 1,3-dioxolane, iso-butyl methyl ketone, ethyl methyl ketone, diethyl ether, tert-butyl methyl ether, tert-butyl ethyl ether, n-pentane, n-hexane, n-heptane, cyclohexane, methylcyclohexane, benzene, toluene, xylene, paraffins, naphtha, mineral oil and petroleum ether fractions.

21. The process according to claim 1, which is conducted under a gas or gas mixture which is inert under the reaction conditions.

22. The process according to claim 21, wherein the gas or gas mixture is a gas mixture with an oxygen content below 10%.

23. The process according to claim 21, wherein the gas or gas mixture comprises at least one member selected from the group consisting of nitrogen, argon, helium, nitrogen/noble gas mixtures, carbon dioxide and carbon monoxide.

24. The process according to claim 1, wherein the catalyst is a tin compound or a tertiary amine.

* * * * *